(12) United States Patent
Takano et al.

(10) Patent No.: US 6,468,780 B2
(45) Date of Patent: Oct. 22, 2002

(54) BACILLUS STRAINS WHICH PRODUCE HMG-COA REDUCTASE INHIBITORS

(75) Inventors: Yutaka Takano; Masaru Hasegawa, both of Hofu (JP); Hideo Mori, Berkeley, CA (US); Katsuhiko Ando, Machida (JP); Keiko Ochiai, Ebina (JP); Hiroaki Motoyama, Yokohama (JP); Akio Ozaki, Hofu (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/829,080

(22) Filed: Apr. 10, 2001

(65) Prior Publication Data

US 2001/0053542 A1 Dec. 20, 2001

Related U.S. Application Data

(62) Division of application No. 09/463,912, filed as application No. PCT/JP98/03396 on Jul. 30, 1998, now Pat. No. 6,245,535.

(30) Foreign Application Priority Data

Aug. 7, 1997 (JP) .............................................. 9-213636

(51) Int. Cl.$^7$ ................................................ C12N 1/20
(52) U.S. Cl. .................... 435/252.5; 435/125; 435/135; 435/136
(58) Field of Search .............................. 435/252.5, 125, 435/135, 136

(56) References Cited

U.S. PATENT DOCUMENTS

| 4,346,227 A | 8/1982 | Terahara et al. ............. 560/119 |
| 5,942,423 A | 8/1999 | Demain et al. .............. 435/125 |

FOREIGN PATENT DOCUMENTS

| EP | 649 907 | 4/1995 |
| EP | 776 974 | 6/1997 |
| WO | WO 96/40863 | 12/1996 |
| WO | WO 98/06867 | 2/1998 |

OTHER PUBLICATIONS

The Journal of Antibiotics, vol. 29, Dec. 1976, pp. 1346–1348.
The Journal of Antibiotics, vol. 36, 1983, pp. 887–891.
Archives of Biochemisrty and Biophysics, vol. 99, 1962, pp. 249–253.

Primary Examiner—Herbert J. Lilling
(74) Attorney, Agent, or Firm—Fitzpatrick, Cella, Harper & Scinto

(57) ABSTRACT

Disclosed is a process for producing a compound represented by general formula (II-a):

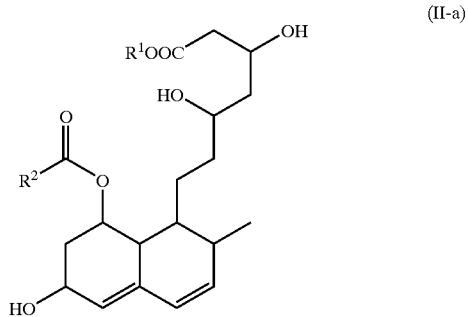

(II-a)

(wherein $R^1$ represents a hydrogen atom, a substituted or unsubstituted alkyl group, or an alkali metal; and $R^2$ represents a substituted or unsubstituted alkyl or aryl group) [hereinafter referred to as Compound (II-a)] or the lactone form of Compound (II-a) [hereinafter referred to as Compound (II-b)] which comprises subjecting a compound represented by general formula (I-a):

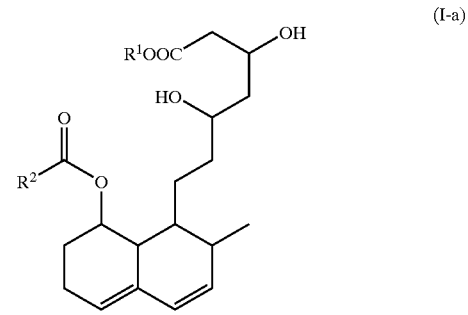

(I-a)

(wherein $R^1$ represents a hydrogen atom, a substituted or unsubstituted alkyl group, or an alkali metal; and $R^2$ represents a substituted or unsubstituted alkyl or aryl group) [hereinafter referred to as Compound (I-a)] or the lactone form of Compound (I-a) [hereinafter referred to as Compound (I-b)] to the action of an enzyme source derived from a microorganism belonging to the genus Bacillus and capable of converting Compound (I-a) or Compound (I-b) into Compound (II-a) or Compound (II-b) in a reaction mixture to form Compound (II-a) or Compound (II-b) in the reaction mixture, and recovering Compound (II-a) or Compound (II-b) from the reaction mixture.

2 Claims, 1 Drawing Sheet

FIG. 1

BACILLUS STRAINS WHICH PRODUCE HMG-COA REDUCTASE INHIBITORS

This application is a division of application Ser. No. 09/463,912 now U.S. Pat. No. 6,245,535 filed Feb. 2, 2000 which is based on PCT/JP98/03396 filed Jul. 30, 1998.

TECHNICAL FIELD

The present invention relates to a process for producing compounds which inhibit hydroxymethylglutaryl-coenzyme A reductase (hereinafter abbreviated as HMG-COA reductase) and have the activity to lower the serum cholesterol level, etc.

BACKGROUND ART

It is known that a compound represented by general formula (VI-a):

(wherein $R^1$ represents a hydrogen atom or an alkali metal) [hereinafter referred to as Compound (VI-a)] or the lactone form of Compound (VI-a) represented by general formula (VI-b):

[hereinafter referred to as Compound (VI-b)] inhibits HMG-COA reductase and exhibits the activity to lower the serum cholesterol level, etc. [The Journal of Antibiotics, 29, 1346 (1976)].

Some microorganisms are known to have the ability to convert a compound represented by general formula (V-a):

(wherein $R^1$ represents a hydrogen atom or an alkali metal) [hereinafter referred to as Compound (V-a)] or the lactone form of Compound (V-a) represented by general formula (V-b):

[hereinafter referred to as Compound (V-b)] into Compound (VI-a) or Compound (VI-b). Such microorganisms include those belonging to the genus Absidia, Cunninghamella, Syncephalasporum or Streptomyces (Japanese Published Unexamined Patent Application No. 50894/82), those belonging to the genus Actinomucor, Circinella, Gongronella, Mortierella, Mucor, Phycomyces, Rhyzopus, Syncephalastrum, Zygorhynchus, Pycnoporus, Rhizoctonia or Nocardia [The Journal of Antibiotics, 36, 887 (1983)], those belonging to the genus Amycolata, Saccharopolyspora, Amycolatopsis or Saccharothrix (Japanese Published Unexamined Patent Application No. 184670/95) and those belonging to the genus Actinomadura (WO96/40863).

The above microorganisms belong to actinomycetes or filamentous fungi. So far, there has not been known a microorganism which belongs to bacteria and has the ability to convert Compound (V-a) or Compound (V-b) into Compound (VI-a) or Compound (VI-b), respectively, like those of the present invention. Actinomycetes and filamentous fungi have the drawback that their growth rate is lower than that of bacteria and thus more time is required for obtaining enough cells for the reaction. Further, there is the problem of controlling the culturing of actinomycetes and filamentous fungi in a fermenter. As actinomycetes and filamentous fungi grow by elongating hyphae, the viscosity of the culture rises as they grow in a fermenter. This often causes shortage of oxygen and makes the culture unhomogenous, which will lower the efficiency of reaction. To solve this problem of oxygen shortage and keep the culture homogenous, the stirring rate of the fermenter must be raised; but hyphae are liable to be cut by stirring at a higher rate, which will lower the activity of microorganisms [Fundamentals of Fermentation Technology, p. 169–190,P.F. Stansbury, A. Whitakaer, Gakkai Shuppan Center (1988)]. Culturing of actinomycetes and filamentous fungi involves such problems. On the other hand, culturing of bacteria, which do not form hyphae, can be readily carried out because the viscosity of the culture hardly rises, and insufficiency of aeration and lack of homogeneity of the culture are seldom observed.

In the DNA recombination technology, expression of genes in bacteria such as *Escherichia coli* is commonly carried out. However, it is generally difficult to efficiently express genes of actinomycetes and filamentous fungi because their codon usage are widely different from those of bacteria such as *Escherichia coli*.

The available tools for efficient expression of genes in actinomycetes, such as vectors and promoters are limited. Therefore, it is desirable to employ bacteria, in which various vectors, promoters, etc. can be used, in order to express genes at a high level and to carry out reactions more efficiently. Any genes from bacteriacan bereadily expressed in bacteria at a high level.

DISCLOSURE OF THE INVENTION

An object of the present invention is to provide a process for producing a compound which inhibits HMG-COA reductase and has the activity to lower the serum cholesterol level, etc.

The present invention relates to a process for producing a compound represented by general formula (II-a):

(II-a)

(II-b)

(wherein $R^1$ represents a hydrogen atom, a substituted or unsubstituted alkyl group, or an alkali metal; and $R^2$ represents a substituted or unsubstituted alkyl or aryl group) [hereinafter referred to as Compound (II-a)] or the lactone form of Compound (II-a) represented by general formula (II-b):

(wherein $R^2$ represents a substituted or unsubstituted alkyl or aryl group) [hereinafter referred to as Compound (II-b)] which comprises subjecting a compound represented by general formula (I-a):

(I-a)

(wherein $R^1$ represents a hydrogen atom, a substituted or unsubstituted alkyl group, or an alkali metal; and $R^2$ represents a substituted or unsubstituted alkyl or aryl group) [hereinafter referred to as Compound (I-a)] or the lactone form of Compound (I-a) represented by general formula (I-b):

(I-b)

(wherein $R^2$ represents a substituted or unsubstituted alkyl or aryl group) [hereinafter referred to as Compound (I-b)] to the action of an enzyme source derived from a microorganism belonging to the genus Bacillus and capable of converting Compound (I-a) or Compound (I-b) into Compound (II-a) or Compound (II-b) in a reaction mixture to form Compound (II-a) or Compound (II-b) in the reaction mixture, and recovering Compound (II-a) or Compound (II-b) from the reaction mixture.

Examples of the alkyl groups include straight-chain or branched alkyl groups having 1–10 carbon atoms, preferably 1–6 carbon atoms, such as methyl, ethyl, propyl, isopropyl, butyl, isobutyl, sec-butyl, tert-butyl, pentyl, neopentyl, hexyl, isohexyl, heptyl, 4,4-dimethylpentyl, octyl, 2,2,4-trimethylpentyl, nonyl and decyl, and branched-chain isomers thereof.

Examples of the aryl group include phenyl and naphthyl.

Examples of the substituent of the substituted alkyl group include halogen, hydroxy, amino, alkoxy, and aryl Examples of the substituent of the substituted aryl group include halogen, hydroxy, amino, alkyl, and alkoxy.

The alkyl moiety of the alkoxy has the same significance as the alkyl group defined above.

The alkali metal means the elements of lithium, sodium, potassium, rubidium, cesium and francium.

Any enzyme source may be used in the present invention as long as it is derived from a microorganism belonging to the genus Bacillus and it has the activity to convert Compound (I-a) or Compound (I-b) into Compound (II-a) orCompound (II-b), respectively. Enzyme sources useful in the invention include microorganisms belonging to the genes Bacillus and having the activity to convert Compound (I-a) or Compound (I-b) into Compound (II-a) or Compound (II-b), cultures or cells of said microorganisms, treated matters thereof, and enzymes extracted from said microorganisms.

Examples of the microorganisms belonging to the genus Bacillus and having the activity to convert Compound (I-a) or Compound (I-b) into Compound (II-a) or Compound (II-b) are those belonging to *Bacillus laterosporus, Bacillus badius, Bacillus brevis, Bacillus alvei, Bacillus circulans, Bacillus macerans, Bacillus megaterium, Bacillus pumilus* and *Bacillus subtilis*.

More specific examples thereof are *Bacillus laterosporus* ATCC 4517, *Bacillus badius* ATCC 14574, *Bacillus brevis* NRRL B-8029, Bacillus sp. PV-6,Bacillus sp. PV-7, *Bacillus alvei* ATCC 6344, *Bacillus circulans* NTCT-2610, *Bacillus macerans* NCIB-9368,*Bacillus megaterium* ATCC 10778, *Bacillus megateriumATCC* 11562,*Bacillus megaterium* ATCC 13402, *Bacillus megateriumATCC* 15177,*Bacillus mecaterium* ATCC 15450, *Bacillus megateriumATCC* 19213,*Bacillus megaterium* IAM 1032, *Bacillus pumilus* FERM BP-2064 and *Bacillus subtilis* ATCC 6051.

Also useful are subcultures, mutants or derivatives of the above microorganisms and recombinants prepared by recombinant DNA techniques. Bacillus sp. PV-6 and Bacillus sp. PV-7 were newly isolated from the soil by the present inventors and the microbiological properties thereof are described below.

PV-6 Strain
(A) Morphological Properties
1. Morphology of cells: Rod Size: 0.8–1.2 ×2.0–4.0 μm
2. Polymorphism of cells: Not observed
3. Motility: Not observed
4. Sporulation : Not observed
(B) Cultural Characteristics
The cultural characteristics of the strain when cultured on a bouillon-agar plate medium and in a bouillon-liquid medium are shown below.
1. Culturing on a bouillon-agar plate medium (1–2 days of culturing)
   1) Growth: Abundant
   2) Color: Cream
   3) Gloss: Observed
   4) Diffusible pigments: Negative
2. Culturing in a bouillon-liquid medium (1–2 days of culturing)
   1) Growth on the surface: None
   2) Turbidity: Positive
3. Stab culture in a bouillon-gelatin medium
   1) Growth: Abundant
   2) Liquefaction of gelatin: Positive
4. Litmus-milk reaction
   1) Reaction: Alkali
   2) Coagulation : Negative
   3) Liquefaction: Negative
(C) Physiological Properties
1. Gram staining: Positive or negative
2. Nitrate reduction: Negative
3. Denitrification reaction: Positive
4. MR test: Negative
5. VP test: Negative
6. Indole production: Negative
7. Hydrogen sulfide production: Positive
8. Hydrolysis of starch: Negative
9. Utilization of citric acid: Positive
10. Utilization of inorganic nitrogen sources
    1) Nitrates: Negative
    2) Ammonium salts: Positive
11. Pigment production: None
12. Urease: Positive
13. Oxidase: Negative
14. Catalase: Positive
15. Growth range
    1) pH: 6–9 (optimum pH: around 7)
    2) Temperature: 6–400° C. (optimum temperature: around 30° C.)
16. Attitude toward oxygen: Aerobic
17. O-F test: Oxidation
18. Acid production (aerobic conditions)

+: Produced –: Not produced

1) L-Arabinose: –
2) D-Xylose: –
3) D-Glucose: +
4) D-Mannose: –
5) D-Fructose: +
6) D-Galactose: –
7) Maltose: –
8) Sucrose: –
9) Lactose: –
10) Trehalose: –
11) D-Sorbitol: –
12) D-Mannitol: +
13) Inositol: –
14) Glycerin: +
15) Starch: –
(D) Chemotaxonomic properties
1. DNA base composition (G+C mol %): 39.1
2. Cellular lipids Major quinone: MK-7 Major fatty acids: anteiso-$C_{5:0}$, iso-$C_{15:0}$
3. Diamino acid contained in the cell wall peptidoglycan: meso-$A_2$pm The strain is an aerobic, nonmotile Gram-positive or negative rod forming endospores. It shows positive catalase activity, negative oxidase activity and positive urease activity, and forms an acid from glucose. It grows at 10° C., but does not grow at 50° C., or higher. It shows the following chemotaxonomic properties: the major quinone is menaquinone-7; the major fatty acids are anteiso-$C_{15:0}$ and iso-$C_{15:0}$; the diamino acid contained in the cell wall peptidoglycan is meso-diaminopimelic acid; and the GC content of DNA is 39.1 mol %.

Figure 1:
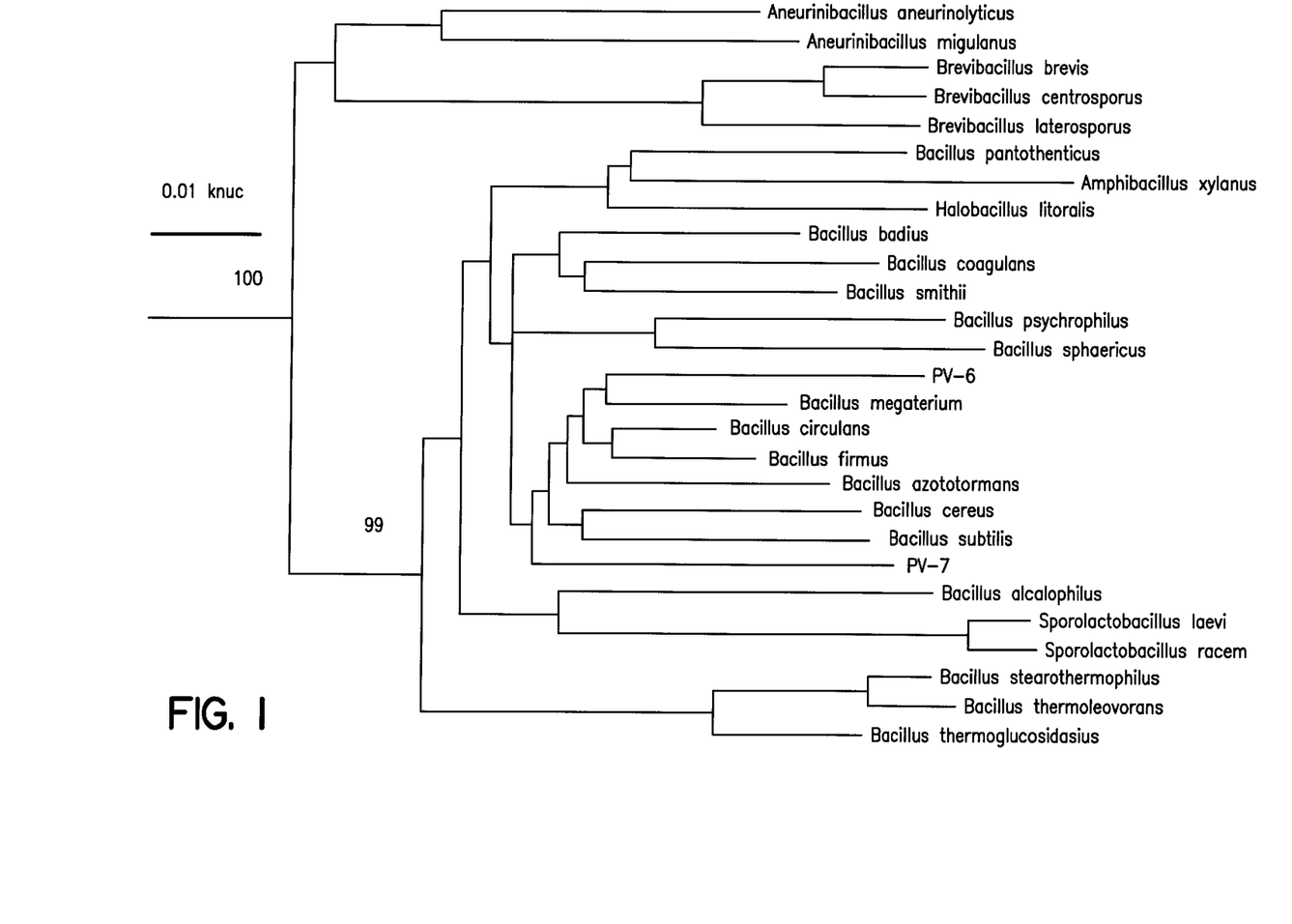
FIG. 1 shows the results of the molecular genealogical analysis of Bacillus sp. PV-6 and Bacillus sp. PV-7 by the neighbor joining method based on the base sequence of 16S rRNA.

Taxonomical studies were made on the strain based on the above microbiological properties referring to the descriptions in Bergey's Manual of Systematic Bacteriology, vol.2 (1986), whereby the strain was presumed to be a bacterium related to the genus Bacillus. Further, molecular genealogical analysis was carried out on the base sequence of 16S rRNA by the neighbor joining method using the base sequences of microorganisms of the genus Bacillus and its related genera as the reference sequences. As a result, the strain was classified in the genus Bacillus by cluster analysis as shown in FIG. 1. The strain was thus identified as a bacterium belonging to the genus Bacillus and was named Bacillus sp. PV-6.

PV-7 Strain
(A) Morphological Properties
1. Morphology of cells: Rod Size: 1.0 ×2.0–3.0 μm
2. Polymorphism of cells: Not observed 3. Motility: Not observed
4. Sporulation: Observed (B) Cultural Characteristics The cultural characteristics of the strain when cultured on a bouillon-agar plate medium and in a bouillon-liquid medium are shown below.

1. Culturing on a bouillon-agar plate medium (1–2 days of culturing)
   1) Growth: Abundant
   2) Color: Ivory
   3) Gloss: None
   4) Diffusible pigments: negative
2. Culturing in a bouillon-liquid medium (1–2 days of culturing)
   1) Growth on the surface: Observed
   2) Turbidity: Positive
3. Stab culture in a bouillon-gelatin medium
   1) Growth: Abundant
   2) Liquefaction of gelatin: Positive
4. Litmus-milk reaction
   1) Reaction: Alkali
   2) Coagulation: Negative
   3) Liquefaction: Negative (C) Physiological Properties 1. Gram staining: Positive or negative
2. Nitrate reduction: Positive on a succinic acid medium
3. Denitrification reaction: Negative
4. MR test: Negative
5. VP test: Negative
6. Indole production: Negative
7. Hydrogen sulfide production: Uncertain
8. Hydrolysis of starch: Negative
9. Utilization of citric acid: Positive
10. Utilization of inorganic nitrogen sources
    1) Nitrates: Positive
    2) Ammonium salts: Positive
11. Pigment production: None
12. Urease: Positive
13. Oxidase: Negative
14. Catalase: Positive
15. Growth range
    1) pH: 6–10 (optimum pH: around 7)
    2) Temperature: 11–47° C. (optimum temperature: around 30° C.)
16. Attitude toward oxygen: Aerobic
17. O-F test: Oxidation
18. Acid production (aerobic conditions)

+: Produced

−: Not produced w: Weakly produced

1) L-Arabinose: +
2) D-Xylose: w
3) D-Glucose: +
4) D-Mannose: w
5) D-Fructose: w
6) D-Galactose: −
7) Maltose: w
8) Sucrose: +
9) Lactose: −
10) Trehalose: w
11) D-Sorbitol: +
12) D-Mannitol: +
13) Inositol: w
14) Glycerin: +
15) Starch: w (D) Chemotaxonomic Properties 1. DNA base composition (G+C mol %): 37.9
2. Cellular lipids
   Major quinone: MK-7
   Major fatty acids: anteiso-$C_{15:0}$, anteiso-$C_{17:0}$
3. Diamino acid contained in the cell wall peptidoglycan: meso-$A_2$pm The strain is an aerobic, nonmotile Gram-positive or negative rod forming endospores. It shows positive catalase activity, negative oxidase activity and positive urease activity, and forms an acid from glucose. It grows at 11° C., but does not grow at 47° C. or higher. It has the following chemotaxonomic properties: the major quinone is menaquinone-7; the major fatty acids are anteiso-$C_{15:0}$ and anteiso-$C_{17:0}$; the diamino acid contained in the cell wall peptidoglycan is meso-diaminopimelic acid; and the GC content of DNA is 37.9 mol %. Taxonomical studies were made on the strain based on the above microbiological properties referring to the descriptions in Bergey's Manual of Systematic Bacteriology, vol.2 (1986), whereby the strain was presumed to be a bacterium related to the genus Bacillus.

Further, molecular genealogical analysis was carried out on the base sequence of 16S rRNA by the neighbor joining method using the base sequences of microorganisms of the genus Bacillus and its related genera as the reference sequences. As a result, the strain was classified in the genus Bacillus by cluster analysis as shown in FIG. 1. The strain was thus identified as the bacterium belonging to the genus Bacillus and was named Bacillus sp. PV-7.

Bacillus sp. PV-6 and Bacillus sp. PV-7 were deposited with the National Institute of Bioscience and Human-Technology, Agency of Industrial Science and Technology, Ministry of International Trade and Industry, 1–3, Higashi 1-chome, Tsukuba-shi, Ibaraki-ken, 305–8566 Japan on Jul. 30, 1997, with accession numbers FERM BP-6029 and FERM BP-6030, respectively.

As the medium for culturing the microorganisms of the present invention, either a synthetic medium or a natural medium may be employed insofar as it contains carbon sources, nitrogen sources, inorganic salts, and the like which can be assimilated by the microorganisms of the invention, and said microorganisms can be efficiently cultured therein. Examples of the carbon sources in the medium include glucose, fructose, glycerol, maltose, starch, saccharose, organic acids such as acetic acid and citric acid, and molasses.

Examples of the nitrogen sources include ammonia, ammonium salts of inorganic acids or organic acids such as ammonium chloride, ammonium sulfate, ammonium acetate, ammonium nitrate and ammonium phosphate, peptone, meat extract, corn steep liquor, casein hydrolysate, soybean meal, Pharmamedia, fish meal, various cells obtained by fermentation and digested matters thereof.

Examples of the inorganic substances include potassium dihydrogenphosphate, dipotassium hydrogenphosphate, magnesium phosphate, magnesium sulfate, sodium chloride, ferrous sulfate, manganese sulfate, copper sulfate, and calcium carbonate.

If necessary, vitamins such as thiamine and biotin, amino acids such as glutamic acid and aspartic acid, nucleic acid-related substances such as adenine and guanine may be added.

It is preferred to culture the microorganisms of the present invention under aerobic conditions, for example, by shaking culture or spinner culture under aeration. In the case of spinner culture under aeration, it is preferred to add an adequate amount of a defoaming agent to prevent foaming. Culturing is usually carried out at 20–40° C., preferably 28–34° C., for 8–120 hours. During the culturing, the pH of the medium is kept at 6.0–10.0, preferably 6.0–7.0. The pH is adjusted using an inorganic or organic acid, an alkaline solution, urea, calcium carbonate, ammonia, etc.

The above microorganisms, cultures or cells of said microorganisms, treated matters thereof, and enzymes extracted from said microorganisms can be used as the enzyme source of the present invention. Examples of the treated matters include cells treated by various means such as drying, freeze-drying, treatment with a surfactant, enzymatic treatment, ultrasonication, mechanical friction and treatment with a solvent, protein-fractionated cells, immobilized cells and immobilized treated cells.

For the conversion of Compound (I-a) or Compound (I-b) into Compound (II-a) or Compound (II-b), Compound (I-a) or Compound (I-b) may be previously added to a medium for culturing the microorganism or may be added to the medium during the culturing. Alternatively, Compound (I-a) or Compound (I-b) may be subjected to the action of an enzyme source obtained by culturing the microorganism in the reaction mixture.

When Compound (I-a) or Compound (I-b) is added to the medium for culturing the microorganism, Compound (I-a) or Compound (I-b) is added to the medium in an amount of 0.1–3 mg/ml, preferably 0.2–1 mg/ml of the medium at the start or in the course of culturing. It is desirable that Compound (I-a) or Compound (I-b) is added to the medium after being dissolved in water or an organic solvent such as methyl alcohol or ethyl alcohol.

When Compound (I-a) or Compound (I-b) is subjected to the action of the enzyme source obtained by culturing the microorganism in the reaction mixture, the amount of the enzyme source to be used varies depending upon the specific activity of said enzyme source, etc. For example, when the culture or cells of the microorganism or a treated matter thereof is used as the enzyme source, the enzyme source is added in an amount of 5–1000 mg/mg, preferably 10–400 mg/mg of Compound (I-a) or Compound (I-b). It is preferred to carry out the reaction in a reaction mixture at 20–40° C., particularly at 28–34° C. The reaction time varies depending upon the amount and specific activity of the enzyme source used, etc., but it is usually 2–150 hours, preferably 72–120 hours.

The reaction mixture may be water, an aqueous medium, an organic solvent, or a mixture of water or an aqueous medium and an organic solvent. The aqueous medium includes buffers such as phosphate buffer, HEPES (N-2-hydroxyethylpiperazine-N-ethanesulfonic acid) buffer, and tris[tris(hydroxymethyl)aminomethane]-hydrochloric acid buffer. As the organic solvent, any organic solvent which does not inhibit the reaction may be used, and examples thereof are acetone, ethyl acetate, dimethyl sulfoxide, xylene, methyl alcohol, ethyl alcohol and butanol. An organic solvent or a mixture of water or an aqueous medium and an organic solvent is preferably used in cases, for example, where Compound (I-b) is used.

When Compound (I-a) or Compound (I-b) is added to the reaction mixture, Compound (I-a) or Compound (I-b) is first a dissolved in water, an aqueous medium, an organic solvent, or a mixture of water or an aqueous medium and an organic solvent in which Compound (I-a) or Compound (I-b) is soluble and then added to the reaction mixture. Any organic solvent which does not inhibit the reaction can be used, and examples thereof are acetone, ethyl acetate, dimethyl sulfoxide, xylene, methyl alcohol, ethyl alcohol and butanol.

Compound (I-b) and Compound (II-b) can be easily converted into Compound (I-a) and Compound (II-a), respectively, by the lactone ring-opening reaction described below. Compound (I-a) and Compound (II-a) can be easily converted into Compound (I-b) and Compound (II-b), respectively, by the lactone-forming reaction described below.

The lactone ring-opening reaction can be carried out, for example, by dissolving Compound (I-b) or Compound (II-b) in an aqueous medium, and adding an acid or an alkali thereto. Examples of the aqueous medium include water and aqueous solutions containing salts which do not inhibit the reaction, such as phosphate buffer and tris buffer. Said aqueous solutions may contain an organic solvent such as methanol, ethanol or ethyl acetate at a concentration which does not inhibit the reaction. Examples of the acid include acetic acid, hydrochloric acid and sulfuric acid, and examples of the alkali include sodium hydroxide, potassium hydroxide and ammonia.

The lactone-forming reaction can be carried out, for example, by dissolving Compound (I-a) or Compound (II-a) in a nonaqueous solvent, and adding an acid or base catalyst thereto. As the nonaqueous solvent, any organic solvent which substantially contains no water and in which Compound (I-a) or Compound (II-a) are soluble can be employed. Examples of the solvent include dichloromethane, chloroform and ethyl acetate. As the catalyst, any catalyst which catalyzes lactonization reaction and does not have any other action than lactonization on substrates and reaction products can be used. Examples of the catalyst include trifluoroacetic acid and p-toluenesulfonic acid. There is no specific restriction as to the reaction temperature, but the reaction is carried out preferably at 0–100° C., more preferably 20–80° C.

In the present invention, Compound (II-a) can be obtained by: (1) subjecting Compound (I-a) to the action of the above enzyme source; (2) first converting Compound (I-b) into Compound (I-a) by the above lactone ring-opening reaction and then subjecting Compound (I-a) to the action of the above enzyme source; or (3) first subjecting Compound (I-b) to the action of the above enzyme source to form Compound (II-b) and then carrying out the above lactone ring-opening reaction.

Similarly, Compound (II-b) can be obtained by: (1) subjecting Compound (I-b) to the action of the above enzyme source; (2) first converting Compound (I-a) into Compound (I-b) by the above lactone-forming reaction and then subjecting Compound (I-b) to the action of the above enzyme source; or (3) first subjecting Compound (I-a) to the action of the above enzyme source to form Compound (II-a) and then carrying out the above lactone-forming reaction.

Compound (II-a) or Compound (II-b) can be recovered from the reaction mixture by methods conventionally used in the organic synthetic chemistry, such as extraction with an organic solvent, recrystallization, thin layer chromatography and high performance liquid chromatography.

For the detection and determination of Compound (II-a) or Compound (II-b) obtained by the present invention, any method by which Compound (II-a) or Compound (II-b) can be detected or determined may be employed. For example, $^{13}$C-NMR spectrum, $^1$H-NMR spectrum, mass spectrum and high performance liquid chromatography (HPLC) can be employed.

There may be stereoisomers such as optical isomers for some of Compounds (I-a), Compounds (I-b), Compounds (II-a) and Compounds (II-b). All possible isomers including these isomers and mixtures thereof are within the scope of the present invention.

Preferred Compounds (I-a) are compounds represented by general formula (III-a):

(III-a)

(wherein R¹ represents a hydrogen atom, a substituted or unsubstituted alkyl group, or an alkali metal; and R² represents a substituted or unsubstituted alkyl or aryl group) [hereinafter referred to as Compounds (III-a)]. More preferred are compounds represented by general formula (V-a):

(V-a)

(wherein R¹ represents a hydrogen atom, a substituted or unsubstituted alkyl group or an alkali metal) [hereinafter referred to as Compounds (V-a)], and particularly preferred are compounds represented by general formula (VII-a):

(VII-a)

(wherein R¹ represents a hydrogen atom, a substituted or unsubstituted alkyl group, or an alkali metal) [hereinafter referred to as Compounds (VII-a)].

Preferred Compounds (I-b) are compounds represented by general formula (III-b):

(III-b)

(wherein R² represents a substituted or unsubstituted alkyl or aryl group) [hereinafter referred to as Compounds (III-b)]. More preferred are compounds represented by general formula (V-b):

(V-b)

[hereinafter referred to as Compounds (V-b)], and particularly preferred is a compound represented by general formula (VII-b):

(VII-b)

[hereinafter referred to as Compound (VII-b)].

Preferred Compounds (II-a) are compounds represented by general formula (IV-a):

(IV-a)

(wherein $R^1$ represents a hydrogen atom, a substituted or unsubstituted alkyl group, or an alkali metal; and $R^2$ represents a substituted or unsubstituted alkyl or aryl group) [hereinafter referred to as Compounds (IV-a)]. More preferred are compounds represented by general formula (VI-a):

(VI-a)

(wherein $R^1$ represents a hydrogen atom, a substituted or unsubstituted alkyl group or an alkali metal) [hereinafter referred to as Compounds VI-a)], and particularly preferred are compounds represented by general formula (VIII-a):

(VIII-a)

(wherein $R^1$ represents a hydrogen atom, a substituted or unsubstituted alkyl group, or an alkali metal) [hereinafter referred to as Compounds (VIII-a)].

Preferred Compounds (II-b) are compounds represented by general formula (IV-b):

(IV-b)

(wherein $R^2$ represents a substituted or unsubstituted alkyl or aryl group) [hereinafter referred to as Compounds (IV-b)]. More preferred are compounds represented by general formula (VI-b):

(VI-b)

[hereinafter referred to as Compounds (VI-b)], and particularly preferred is a compound represented by general formula (VIII-b):

(VIII-b)

[hereinafter referred to as Compound (VIII-b)].

Examples of the present invention are shown below.

BEST MODES FOR CARRYING OUT THE INVENTION

EXAMPLE 1

In 9.5 ml of methanol was dissolved 100 mg of Compound (VII-b) (Sigma Chemical Co.), and 0.5 ml of 1 Nsodiumhydroxide was added thereto, followed by shaking at room temperature for one hour. The resulting mixture was concentrated to dryness, and 5 ml of deionized water was added thereto. The resulting solution was adjusted to pH 6.5–7.5 by addition of about 0.1 ml of 1 N hydrochloric acid, and 4.9 ml of deionized water was added thereto to give 10 ml of a solution of Compound (VII-a-1) [Compound (VII-a) in which $R^1$ is sodium] having a final concentration of 10 mg/ml.

Each of *Bacillus laterosporus* ATCC 4517, *Bacillus badius* ATCC 14574, *Bacillus brevis* NRRL B-8029, Bacillus sp. PV-6 and Bacillus sp. PV-7 was spread on an agar medium [1% peptone (Kyokuto Pharmaceutical Ind. Co., Ltd.), 0.7% meat extract (Kyokuto Pharmaceutical Ind. Co., Ltd.), 0.3% NaCl (Nacalai Tesque, Inc.) and 2% bactoagar (Difco Laboratories Inc.); adjusted to pH 7.2 with 1 N sodium hydroxide], and cultured at 30° C. for 24 hours. One loopful of each strain grown on the agar medium was inoculated into an A-spitz tube containing 3 ml of C medium [2% glucose (Nacalai Tesque, Inc.), 1% meat extract (Kyokuto Pharmaceutical Ind. Co., Ltd.), 1% yeast extract (Oriental Yeast Co., Ltd.) and 0.1% peptone (Kyokuto Pharmaceutical Ind. Co., Ltd.)] adjusted to pH 7.5 followed by shaking culture at 30° C. for 24 hours. Then, 0.06 ml of the resulting culture was inoculated into a 15-ml A-spitz tube (16.5 ×115 mm, Iuchi Seieido) containing 3 ml of C medium adjusted to pH 7.5,followed by shaking culture at 30° C. Twenty-four hours after the start of culturing, the above Compound (VII-a-1) was added to the A-spitz tube to the final concentration of 0.2 mg/ml. To the culture was added glucose 24 hours and 72 hours after the addition of Compound (VII-a-l) to the final concentration of 1%, respectively. The reaction was carried out for 120 hours in total.

After the completion of reaction , the reaction mixture was adjusted to pH 4 with acetic acid (Nacalai Tesque, Inc.). To 1 ml of the resulting mixture was added 2 ml of ethyl acetate (Nacalai Tesque, Inc.), followed by shaking for one hour. Then, the mixture was centrifuged using a centrifuge (Hitachi Koki Co., Ltd.,; 05P-21 type) at 3000 rpm for 5 minutes to obtain the ethyl acetate layer as the supernatant. After the solvent was removed from the supernatant with a centrifugal evaporator (Tommy Seiko Co., Ltd.,; CC-101 type), the residue was dissolved in 1 ml of methanol. Then, a portion of this methanol solution was subjected to HPLC analysis [column: Inertsil ODS-2 (5 μm, 4×250 mm, GL Sciences), column temperature: 60° C., mobile phase: acetonitrile:water:phosphoric acid=55:45:0.05,flow rate: 0.9 ml/min, detection wavelength: 237 nm]. As a result, it was confirmed from the retention time that Compound (VIII-a-1) [Compound (VIII-a) in which $R^1$ is sodium] was formed. Under the above conditions, the retention time of Compound (VII-a-1) is 2.36 minutes and that of Compound (VIII-a-1) is 6.51 minutes. The peak corresponding to Compound (VIII-a-1) was observed with all the strains used in the experiment. For example, the reaction product obtained by using *Bacillus brevis NRRL B-8029* showed peaks at 2.36 minutes and 6.47 minutes.

The amounts of Compound (VIII-a-1) obtained by using the respective strains were as follows: *Bacillus laterosporus* ATCC 4517, 16.8 mg/l; *Bacillus badius* ATCC 14574, 10.3 mg/l; *Bacillus brevis* NRRL B-8029, 1.4 mg/l; Bacillus sp. PV-6, 7.3 mg/l; and Bacillus sp. PV-7, 42.0 mg/l.

EXAMPLE 2

Bacillus sp. PV-7 was spread on the same agar medium as used in Example 1,and cultured at 30° C. for 24 hours. One loopful of the strain grown on the agar medium was inoculated into two 15-ml A-spitz tubes (16.5×115 mm, Iuchi Seieido) each containing 3 ml of C medium adjusted to pH 7.5, followed by shaking culture at 30° C. for 24 hours. The resulting culture was inoculated in 0.06 ml portions into sixty 15-ml A-spitz tubes each containing 3 ml of C medium adjusted to pH 7.5, followed by shaking culture at 30° C. Twenty-four hours after the start of culturing, Compound (VII-a-1) obtained in the same manner as in Example 1 was added to each of the tubes to the final concentration of 0.4 mg/ml, and glucose was added thereto 24 hours and 72 hours after the start of culturing to the final concentration of 1%, respectively. The culturing was carried out for 120 hours in total. After the completion of culturing, the culture was centrifuged at 3000 rpm at 4° C. for 10 minutes to separate the supernatant. The obtained supernatant was adjusted to pH 4.0 with acetic acid, and 360 ml of ethyl acetate was added thereto, followed by shaking at 30° C. for one hour. The resulting mixture was allowed to stand to separate the supernatant. To the obtained supernatant was added 90 ml of deionized water, followed by shaking at 30° C. for 30 minutes. Then, the supernatant was obtained again and 90 ml of a saturated aqueous solution of sodium chloride was added thereto. After shaking at 30° C. for minutes, the supernatant was separated.

To the obtained supernatant was added 4.5 g of anhydrous $Na_2SO_4$, and the resulting mixture was allowed to stand at room temperature for 15 minutes, dehydrated, and then concentrated to dryness under reduced pressure. The residue was dissolved in 5 ml of deionized water, and the resulting solution was adjusted to pH 9.0 with sodium hydroxide and then passed through HP-20 column (100 ml, 35×100 mm, Mitsubishi Chemical Corporation). After the column was washed with 300 ml of deionized water, elution was carried out with 120 ml of a 45% aqueous solution of acetone. The eluate was taken infractions and subjected to HPLC analysis [analysis column: Inertsil ODS-2 (5μm, 4×250 mm, GL Sciences, column temperature: 60° C., mobile phase: acetonitrile: water: phosphoric acid=55:45:0.05, flow rate: 0.9 ml/min, detection wavelength: 237 nm] to collect a fraction containing Compound (VIII-a-1). After removal of acetonitrile under reduced pressure, the fraction was adjusted to pH 4.0 with acetic acid, and 360 ml of ethyl acetate was added thereto, followed by shaking at 30° C. for one hour. The resulting mixture was allowed to stand to separate the supernatant. To the obtained supernatant was added 90 ml of deionized water, followed by shaking at 30° C. for 30 minutes. Then, the supernatant was obtained again and 90 ml of a saturated aqueous solution of sodium chloride was added thereto. After shaking at 30° C. for 30 minutes, the supernatant was separated.

To the obtained supernatant was added 4.5 g of anhydrous $Na_2SO_4$, and the resulting mixture was allowed to stand at room temperature for 15 minutes, dehydrated, and then concentrated to dryness under reduced pressure. The residue was dissolved in dichloromethane, and 1% of trifluoroacetic acid was added thereto for lactonization. The reaction mixture was purified by preparative HPLC [column: Develosil ODS-HG-5 (20×250 mm, Nomura Chemical Co., Ltd.), column temperature: 40° C., solvent: 55% methanol, flow rate: 20 ml/min, detection wavelength: 237 nm] to give 5.1 mg of Compound (VIII-b).

The results of mass spectrometry and $^1$H-NMR analysis of the obtained Compound (VIII-b) are shown below.

Mass spectrum

The measurement was carried out using a mass spectrometer (JEOL Ltd., JMS-HX/HX110A) and by the use of m-nitrobenzyl alcohol as a matrix in the positive mode. As a result, the pseudo molecular ion peak ([M+H]+) was observed at m/z 407,which agreed with the value expected from the structure and the molecular weight (406) of Compound (VIII-b).

$^1$H-NMR spectrum

The measurement was carried out using a spectrometer (JEOL Ltd., JNM-α400) and by the use of TMS as an internal standard in chloroform-d at 400MHz. The result is shown below. The obtained spectrum data agreed with the known data on Compound (VIII-b) [Annual Report of Research Laboratories of Sankyo Co., Ltd., 37, 147(1985)].

δppm (CDCl$_3$): 6.01(1H, d, J=9.5Hz), 5.89(1H, dd, J=9.5, 5.9Hz), 5.58(1H, m), 5.41(1H, m), 4.60(1H, dddd, J=10.6, 7.3, 5.4, 2.8Hz), 4.40(1H, m), 4.38(1H, m), 2.74(1H, dd, J=17.6, 5.1Hz), 2.61(1H, ddd, J=17.6, 3.7, 1.5Hz), 2.59(1H, dddd, J=13.1, 6.0, 4.8, 1.5Hz), 2.40(1H, m), 2.36(1H, m), 2.34(1H, m), 1.95(1H, dddd, J=14.4, 3.7, 2.9, 1.7Hz), 1.86 (1H, dddd, J=12.5, 12.3, 7.3, 4.3Hz), 1.69(1H, m), 1.68(1H, m), 1.64(1H, m), 1.57(1H,m), 1.5–1.4(2H, m), 1.43(1H, m), 1.30(1H, m), 1.12(3H, d, J=6.8Hz), 0.91(3H, d, J=7.1Hz), 0.89(3H,t, J=7.4Hz)

EXAMPLE 3

Compound (VII-a-1) [Compound (VII-a) in which R$^1$ is sodium] was obtained in the same manner as in Example 1.

Each of *Bacillus alvei* ATCC 6344, *Bacillus circulans* NTCT-2610, *Bacillus macerans* NCIB-9368, *Bacillus megaterium* ATCC 10778, *Bacillus megaterium* ATCC 11562, *Bacillus megaterium* ATCC 13402, *Bacillus megaterium* ATCC 15177, *Bacillus megaterium* ATCC 15450, *Bacillus megaterium* ATCC 19213, *Bacillus megaterium* IAM 1032, *Bacillus pumilus* FERM BP-2064 and *Bacillus subtilis* ATCC 6051 was spread on an agar medium [1% peptone (Kyokuto Pharmaceutical Ind. Co., Ltd.), 0.7% meat extract (Kyokuto Pharmaceutical Ind. Co., Ltd.), 0.3% NaCl (Nacalai Tesque, Inc.) and 2% bactoagar (Difco Laboratories Inc.); adjusted to pH 7.2 with 1 N sodium hydroxide], and cultured at 30° C. for 24 hours. One loopful of each strain grown on the agar medium was inoculated into a test tube (13×165 mm) containing 3 ml of LBG medium [2% glucose (Nacalai Tesque, Inc.), 1% bactotryptone (Difco Laboratories Inc.), 0.5% yeast extract (Difco Laboratories Inc.) and 0.5% NaCl (Nacalai Tesque, Inc.); adjusted to pH 7.4], followed by shaking culture at 30° C. for 24 hours. Then, 0.2 ml of the resulting culture was inoculated into a test tube (21×200 mm) containing 10 ml of LBGCa medium [2% glucose (Nacalai Tesque, Inc.), 1% bactotryptone (Difco Laboratories Inc.), 0.5% yeast extract (Difco Laboratories Inc.), 0.5% NaCl (Nacalai Tesque, Inc.) and 0.5% calcium carbonate (Kokusan Chemical Works Co., Ltd.); adjusted to pH 7.4], followed by shaking culture at 30° C. After 24 hours of culturing, 1 ml of the culture was put into a 13-ml polypropylene tube (SARSTEDT Co., Ltd., imported by Assist Co., Ltd., No. 60 540S), and Compound (VII-a-1) and glucose were added thereto to the final concentrations of 0.2 mg/ml and 1%, respectively, followed by reaction for 48 hours.

After the completion of reaction , the reaction mixture was adjusted to pH 4 with acetic acid (Nacalai Tesque, Inc.). To 1 ml of the resulting mixture was added 2 ml of ethyl acetate (Nacalai Tesque, Inc.), followed by shaking for one hour. Then, the mixture was centrifuged using a centrifuge (Hitachi Koki Co., Ltd., ; 05P-21 type) at 3000 rpm for 5 minutes to obtain the ethyl acetate layer as the supernatant. After the solvent was removed from the supernatant with a centrifugal evaporator (Tommy Seiko Co., Ltd., CC-101), the residue was dissolved in 1 ml of methanol. Then, a portion of this methanol solution was subjected to HPLC analysis [column: Inertsil ODS-2 (5 μm, 4×250 mm, GLSciences), column temperature: 60° C., mobile phase: acetonitrile:water:phosphoric acid=55:45:0.05, flow rate: 0.9 ml/min, detection wavelength: 237 nm]. As a result, it was confirmed from the retention time that Compound (VIII-a-1) [Compound (VIII-a) in which R$^1$ is sodium] was formed.

The amounts of Compound (VIII-a-1) obtained by using the respective strains were as follows: *Bacillus alvei* ATCC 6344, 0.18 mg/l; *Bacillus circulans* NTCT-2610, 0.18 mg/l; *Bacillus macerans* NCIB-9368, 0.32 mg/l; *Bacillus megaterium* ATCC 10778, 8.4 mg/l; *Bacillus megaterium* ATCC 11562, 0.31 mg/l; *Bacillus megaterium* ATCC 13402, 1.30 mg/l; *Bacillus megaterium* ATCC 15177, 1.60 mg/l; *Bacillus megaterium* ATCC 15450, 0.58 mg/l; *Bacillus megaterium* ATCC 19213, 0.16 mg/l; *Bacillus megaterium* IAM 1032, 9.20 mg/l; *Bacillus pumilus* FERM BP-2064, 0.17 mg/l; and *Bacillus subtilis* ATCC 6051, 1.11 mg/l.

EXAMPLE 4

*Bacillus laterosporus* ATCC 4517 was spread on the same agar medium as used in Example 1,and cultured at 30° C. for 24 hours. One loopful of the strain grown on the agar medium was inoculated into two 15-ml A-spitz tubes (16.5× 115 mm, Iuchi Seieido) each containing 3 ml of C medium adjusted to pH 7.5, followed by shaking culture at 30° C. for 24 hours. The resulting culture was inoculated in 0.06 ml portions into sixty 15-ml A-spitz tubes each containing 3 ml of C medium adjusted to pH 7.5,followed by shaking culture at 30° C. Twenty-four hours after the start of culturing, Compound (VII-a-1) obtained in the same manner as in Example 1 was added to each of the tubes to the final concentration of 0.4 mg/ml and glucose was added thereto 24 hours and 72 hours after the start of culturing to the final concentration of 1%, respectively. The culturing was carried out with shaking for 120 hours in total. After the completion of culturing, the culture was centrifuged at 3000 rpm at 4° C. for 10 minutes to separate the supernatant. The obtained was adjusted to pH 3.0 with 1 N hydrochloric acid. After 360 ml of ethyl acetate was added thereto, the mixture was shaken and then allowed to stand to separate the supernatant. This treatment was repeated 3 times. To the obtained supernatant was added 90 ml of deionized water, followed by shaking. Then, the supernatant was obtained again and 90 ml of a saturated aqueous solution of sodium chloride was added thereto. After shaking, the supernatant was separated.

To the obtained supernatant was added 4.5 g of anhydrous Na$_2$SO$_4$, and the mixture was allowed to stand at room temperature for 15 minutes, dehydrated, and then concentrated to dryness under reduced pressure. The residue was dissolved in 5 ml of deionized water, and the resulting solution was adjusted to pH 9.0 with sodium hydroxide and then passed through HP-20 column (50 ml, 25×100 mm, Mitsubishi Chemical Corporation). After the column was washed with 150 ml of deionized water, elution was carried out stepwise using 100 ml each of 20%, 30% and 40% aqueous solutions of acetone. The eluate was taken in fractions and subjected to HPLC analysis [analysis column: Inertsil ODS-2 (5μm, 4×250 mm, GL Sciences), column temperature: 60° C., mobile phase: acetonitrile:water:phosphoric acid=55:45:0.05, flow rate: 0.9ml/min, detection wavelength: 237 nm] to collect a fraction containing Compound (VIII-a-1) based on the retention time. After removal of acetonitrile under reduced pressure, the fraction was adjusted to pH 3.0 with 1 N hydrochloric acid, and 360 ml of ethyl acetate was added thereto, followed by shaking. The resulting mixture was allowed to stand to separate the supernatant. To the obtained supernatant was added 90 ml of deionized water, followed by shaking. Then, the supernatant was obtained again and 90 ml of a saturated aqueous solution of sodium chloride was added thereto. After shaking, the supernatant was separated.

To the obtained supernatant was added 4.5 g of anhydrous $Na_2SO_4$, and the mixture was allowed to stand at room temperature for 15 minutes, dehydrated, and then concentrated to dryness under reduced pressure. The residue was dissolved in dichloromethane, and 1% trifluoroacetic acid was added thereto for lactonization. The reaction mixture was purified by preparative TLC [silica gel plate: No. 1.05744 (200×200 mm, 0.5 mm thick), MERCK Co. Inc., developer: ethyl acetate, color developer: 12.5% phosphomolybdenic acid and 1% cerium sulfate/ solution in 10% sulfuric acid] to give 0.8 mg of Compound (VIII-b). The results of mass spectrometry and $^1$H-NMR analysis of the obtained Compound (VIII-b) are shown below.

Mass Spectrum

The measurement was carried out using a mass spectrometer (JEOL Ltd., JMS-HX/HX110A) and by the use of m-nitrobenzyl alcohol as a matrix in the positive mode. As a result, the pseudo molecular ion peak ([M+H]$^+$) was observed at m/z 407,which agreed with the value expected from the structure and the molecular weight (406) of Compound (VIII-b).

Further, as a result of high resolution FAB MS measurement, the pseudo molecular ion peak ([M+H]$^+$) was observed at m/z 407.2440,which agreed with the calculated value (m/z 407.2434: $C_{23}H_{35}O_6$) expected from the molecular formula ($C_{23}H_{34}O_6$) of the compound within the limit of the measurement error.

$^1$H-NMR Spectrum

The measurement was carried out using a nuclear magnetic resonance spectrometer (JEOL Ltd., JNM-LA300) and by the use of chloroform (δ 7.26 ppm) as an internal standard in chloroform-d at 300 MHz. The result is shown below. The obtained spectrum data agreed with the known data on Compound (VIII-b) [Annual Report of Research Laboratories of Sankyo Co., Ltd., 37, 147 (1985)].

δ ppm (CDCl$_3$): 6.00(1H, d, J=9.7Hz), 5.90(1H, dd, J=9.7, 5.7Hz), 5.58(1H, m), 5.41(1H, m), 4.61(1H, dddd, J=10.9, 7.8, 5.1, 2.9Hz), 4.45–4.35(1H, m), 4.38(1H, dq, J=5.0, 3.9Hz), 2.73(1H, dd, J=17.6, 5.0 Hz), 2.62(1H, ddd, J=17.6, 3.9, 1.7Hz), 2.59(1H, dddd, J=13.5, 6.6, 4.8, 1.6Hz), 2.45–2.35(1H, m), 2.36(1H, sex, J=6.9Hz), 2.40–2.30(1H, m), 1.95(1H, dddd, J=14.4, 3.9, 2.9, 1.7Hz), 1.90–1.80(1H, m), 1.75–1.60(1H, m), 1.68(1H, ddd, J=14.4, 10.9, 3.9Hz), 1.65(1H, dqu, J=13.6, 7.5Hz), 1.65–1.50(1H, m), 1.43(1H, dqu, J=13.6, 7Hz), 1.50–1.35(2H, m), 1.35–1.25(1H, m), 1.12(3H, d, J=7.0 Hz), 0.91(3H, d, J=7.0Hz), 0.89(3H, t, J=7.4Hz)

INDUSTRIAL APPLICABILITY

The present invention provides an efficient process for producing a compound which inhibits HMG-COA reductase and has the activity to lower the serum cholesterol level, etc.

What is claimed is:

1. An isolated strain of Bacillus sp. PV-6 (FERM BP-6029).

2. An isolated strain of Bacillus sp. PV-7 (FERM BP-6030).

* * * * *